United States Patent [19]

Gramltch et al.

[11] Patent Number: 4,761,489

[45] Date of Patent: Aug. 2, 1988

[54] SUBSTITUTED 5-FORMYL-1,3-DIOXEPANS

[75] Inventors: Walter Gramlich, Edingen-Neckarhausen; Hardo Siegel, Speyer; Dieter Jahn, Edingen-Neckarhausen, all of Fed. Rep. of Germany

[73] Assignee: BASF Aktiengesellschaft, Rheinland-Pfalz, Fed. Rep. of Germany

[21] Appl. No.: 924,762

[22] Filed: Oct. 30, 1986

[30] Foreign Application Priority Data

Nov. 7, 1985 [DE] Fed. Rep. of Germany ....... 3539468

[51] Int. Cl.$^4$ ............................................. C07D 321/06
[52] U.S. Cl. ................................... 549/347; 549/333; 512/9; 512/12
[58] Field of Search ................. 549/333, 347; 252/522

[56] References Cited

U.S. PATENT DOCUMENTS

| 3,117,134 | 1/1964 | Sterling et al. | 549/333 |
| 3,769,303 | 10/1973 | Easter et al. | 549/347 |
| 3,822,290 | 7/1974 | Tavares et al. | 549/347 |
| 3,822,291 | 7/1974 | Tavares et al. | 549/347 |
| 3,985,769 | 10/1976 | Vesley et al. | 549/347 |
| 4,031,140 | 6/1977 | Schreiber et al. | 549/347 |
| 4,248,787 | 2/1981 | Sprecker et al. | 549/347 |

FOREIGN PATENT DOCUMENTS

| 557949 | 5/1958 | Canada | 549/347 |
| 0085937 | 8/1983 | European Pat. Off. | |
| 1816042 | 6/1970 | Fed. Rep. of Germany | |
| 2407863 | 9/1974 | Fed. Rep. of Germany | |
| 21479 | 7/1975 | Japan | 549/347 |

OTHER PUBLICATIONS

J. Falbe, Carbon Monoxide in Organic Synthesis, Springer-Verlag (1970) pp. 35–36.

Chemical Abstracts, vol. 66:55590k (1967).

Primary Examiner—Norma S. Milestone
Attorney, Agent, or Firm—Oblon, Fisher, Spivak, McClelland & Maier

[57] ABSTRACT

Substituted 5-formyl-1,3-dioxepans of the general formula I

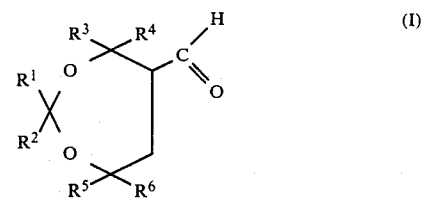

where $R^1$ is a straight-chain or branched alkyl radical of 1 to 10 carbon atoms which may furthermore contain oxygen in the form of an ether group, or a 5-membered to 8-membered ring which is unsubstituted or substituted by alkyl groups and/or an alkylene group, has up to 10 carbon atoms and may furthermore contain oxygen in the form of an ether group, $R^2$ is hydrogen, or $R^1$ and $R^2$ together form an alkylene radical of 4 to 10 carbon atoms which is unsubstituted or substituted by alkyl or alkoxy and may furthermore contain oxygen in the form of an ether group, and $R^3$, $R^4$, $R^5$ and $R^6$ are each hydrogen or methyl, and the total number of carbon atoms is not more than 25, their preparation and their use as scents. Particularly interesting compounds are 2-tert-butyl-5-formyl-1,3-dioxepan, 2-isopropyl-5-formyl-1,3-dioxepan, 2-pentyl-4,7-dimethyl-5-formyl-1,3-dioxepan, 2-(2,4,4-trimethylpentyl)-5-formyl-1,3-dioxepan, 9-formyl-7,12-dioxaspiro[5,6]dodecane and 2,4,4,7,7-pentamethyl-5-formyl-1,3-dioxepan.

7 Claims, No Drawings

SUBSTITUTED 5-FORMYL-1,3-DIOXEPANS

The present invention relates to substituted 5-formyl-1,3-dioxepans of the general formula I

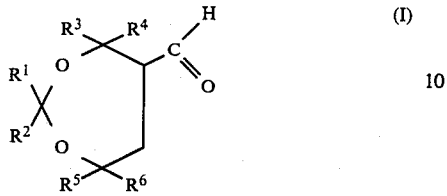

where $R^1$ is a straight-chain or branched alkyl radical of 1 to 10 carbon atoms which may furthermore contain oxygen in the form of an ether group, or a 5-membered to 8- membered ring which is unsubstituted or substituted by alkyl groups and/or an alkylene group, has not more than 10 carbon atoms and may furthermore contain oxygen in the form of an ether group, preferably a straight-chain or branched alkyl radical of 1 to 8 carbon atoms, $R^2$ is hydrogen, or $R^1$ and $R^2$ together form an alkylene radical of 4 to 10 carbon atoms which is unsubstituted or substituted by lower alkyl or alkoxy and may furthermore contain oxygen in the form of an ether group, preferably an alkylene radical of 4 to 6 carbon atoms, and $R^3$, $R^4$, $R^5$ and $R^6$ are each hydrogen or methyl, and the total number of carbon atoms is not more than 25.

Because of the general lack of availability of many natural scent components, the necessity of adapting to changing tastes in fashion and the steadily growing demand for odor improvers for products in daily use, such as cleaning agents, cosmetics, glues, etc., the scent industry is in constant need of novel scents which, alone or in the form of compositions, constitute useful perfumes or fragrance materials with interesting notes. Because little is known about the relationship between structure and fragrance properties, the selective synthesis of scents having the desired olfactory properties is not possible; hence, it is necessary to provide compounds which have useful fragrance properties.

We have found, by chance, that the compounds described above, of the formula I, constitute a novel class having very interesting notes.

The present invention therefore also relates to the use of the substituted 5-formyl-1,3-dioxepans of the general formula I as scents, and to scent compositions containing these dioxepans, preferably in an amount of from 1 to 50% by weight, based on the total composition.

The present invention furthermore relates to a process for the preparation of the compounds of the general formula I, wherein A. a carbonyl compound of the general formula II

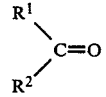

where $R^1$ and $R^2$ have the meanings stated in claim 1, or one of its acetals or ketals, is subjected to a cyclization reaction with an alkenediol of the general formula III

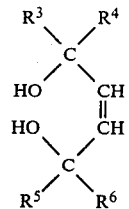

where $R^3$, $R^4$, $R^5$ and $R^6$ have the meanings stated in claim 1, in the presence of an acidic catalyst, and B. the resulting substituted 4,7-dihydro-1,3-dioxepin of the general formula IV

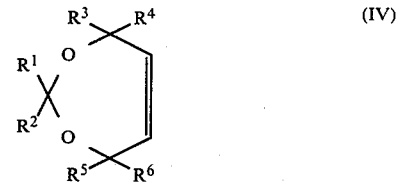

is hydroformylated in a conventional manner.

Suitable carbonyl compounds of the formula II are formaldehyde ($R^1=R^2=$hydrogen), aliphatic aldehydes ($R^1=$hydrogen and $R^2=$alkyl) and cycloaliphatic ketones.

Examples of aldehydes are acetaldehyde, propionaldehyde, 2-methylpropanol, n-butyraldehyde, 2-methylbutanal, 3-methylbutanal, 3-ethylbutanal, valeraldehyde, 2-methylpentanal, 3-methylpentanal, 4-methylpentanal, 2,2-dimethylpropanal (pivalaldehyde) and unsubstituted higher aldehydes, such as n-hexanal, n-heptanal, n-octanal, n-nonanal, decanal and their mono-alkylated and/or polyalkylated derivatives. The most well known members of this group are the large-scale chemical product 2-ethylhexanal and 3,5,5-trimethylhexanal.

Examples of oxygen-containing carbonyl components are methoxyacetaldehyde, 3-isobutoxypropanal, methoxyacetone and methoxybutanone.

Examples of carbonyl compounds which contain 5-membered to 8-membered rings which have not more than 10 carbon atoms and may contain oxygen are cyclohexanecarbaldehyde, tetrahydropyran-2-carbaldehyde, tetrahydropyran-3-carbaldehyde and 2,7,7-trimethylbicyclo[3.1.1$^{1.5}$]heptane-3-carbaldehyde.

Examples of suitable cyclic ketones in which $R^1$ and $R^2$ form part of a 5-membered to 8-membered ring which has not more than 10 carbon atoms and may contain oxygen are cyclopentanone (5 carbon atoms), 2,4,4-trimethylcyclopentanone (8 carbon atoms), cyclohexanone, 2,3,6-trimethylcyclohexanone (9 carbon atoms), cycloheptanone and cyclooctanone.

Examples of suitable alkenediols of the general formula III are but-2-ene-1,4-diol, pent-2-ene-1,4-diol, hex-3-ene-2,5-diol, 4-methylpent-2-ene-1,4-diol, 2-methylhex-3-ene-2,5-diol and 2,5-dimethylhex-3-ene-2,5-diol.

The stated alkenediols can be readily prepared by partial hydrogenation of the corresponding alkynediols using Lindlar catalysts, or are themselves large-scale industrial products or intermediates, such as but-2-ene-1,4-diol, which can be obtained by reacting acetylene with formaldehyde in a molar ratio of 1:2 and subjecting the resulting but-2-yne-1,4-diol to partial hydrogenation. 2,5-dimethylhex-3-yne-2,5-diol can be readily prepared by reacting acetylene and acetone (cf. German Published Application DAS No. 1,816,042).

The readily available carbonyl compounds of the formula II are subjected to a cyclization reaction with the alkenediols of the formula III in reaction step A in the presence of a conventional acidic catalyst, such as p-toluenesulfonic acid, and in general an entraining agent, such as toluene or cyclohexane, with removal of water. Acetalation of the carbonyl compounds with a lower alcohol prior to cyclization did not generally prove more advantageous than cyclization of the carbonyl compounds themselves.

The alkylated 4,7-dihydro-1,3-dioxepins of the formula IV which are obtained in the cyclization, the majority of which are novel, are hydroformylated exclusively to the 5-formyl-1,3-dioxepans of the formula I.

The hydroformylation is carried out in a conventional manner (cf. for example J. Falbe, Carbon Monoxide in Organic Synthesis, Springer-Verlag 1970, in particular page 35).

A particularly suitable catalyst for the hydroformylation reaction is rhodium in the form of a finely divided metal, an oxide or a salt of an organic or inorganic acid, in the presence or absence of a tertiary phosphine or phosphite in up to a 300-fold excess, based on rhodium. Other suitable catalysts are rhodium carbonyl compounds or rhodium complexes which are obtained by reacting rhodium salts or rhodium carbonyl compounds with phosphine or phosphites and olefins or polyunsaturated olefins. In the case of these complexes too, phosphines and phosphites may be present in up to 300-fold excess, based on rhodium.

The catalysts may be used in homogeneous or heterogeneous form (for example on carriers).

The catalyst concentration corresponds to 1–1000 ppm of rhodium, based on the substrate used.

Carbon monoxide and hydrogen are preferably used in about equimolar amounts, although it is possible to use either of the gases in up to about 4-fold molar excess.

Hydroformylation is preferably carried out at from 70° to 150° C. and under a total carbon monoxide/hydrogen pressure of from 10 to 700 bar, in the presence or absence of an inert solvent or diluent, such as benzene, toluene, a xylene mixture, naphtha, an ether or an ester.

It may be carried out continuously or batchwise.

The reaction mixture can be worked up in a conventional manner, for example by distillation, to obtain the product. The resulting alkylated 5-formyl-1,3-dioxepans of the formula I constitute a very interesting novel class of scents possessing different, characteristic novel notes.

For example, the compound 2-tert-butyl-5-formyl-1,3-dioxepan, which is readily obtainable by reacting pivalaldehyde with but-2-ene-1,4-diol and then subjecting the product to hydroformylation, has a very interesting combination of smells which is reminiscent both of the freshness of the sea and of lily of the valley.

2-isopropyl-5-formyl-1,3-dioxepan has only one methyl group less than the tert-butyl compound but possesses a completely different, green woody scent.

The 2-n-propyl homolog on the other hand has a fine sweet spicy estragole note.

If n-hexanal is reacted with but-2-ene-1,4-diol and the cyclization product is hydroformylated, the product obtained is 5-formyl-2-pentyl-1,3-dioxepan, which has a very interesting herbaceous green note reminiscent of rhubarb.

The overview, in tabulated form, of the olfactory properties of the most important novel compounds illustrates the great variety and importance of these compounds and also shows what surprisingly great changes in scent are produced by small changes in the molecule.

Where $R^1$ and $R^2$ have different meanings, the compounds according to the invention occur as E/Z diastereomer mixtures (in general 1:1 mixtures). It is possible to increase the concentration of one of the diastereomers by distillation.

The compounds according to the invention can therefore occur in stereoisomeric forms, both as diastereomers and as enantiomers.

The position of the formyl group in the dioxepan ring is important with regard to the olfactory properties. Dioxepans which are otherwise identical but carry the formyl group in the 4- or 7-position instead of the 5-position exhibited very poor olfactory properties in every case investigated, so that they are unimportant as scents.

The substituted 5-formyl-1,3-dioxepans according to the invention can readily be combined with other scents in various ratios to give novel, interesting scent compositions.

Apart from fine perfumery, such compositions can also be used for perfuming cosmetics such as creams, lotions, aerosols, toilet soaps and industrial articles, such as cleaning agents, detergents, softeners, disinfectants and textile treatment agents.

Substituted 5-formyl-1,3-dioxepans of the general formula I where $R^1$ is a straight-chain or branched alkyl radical of 1 to 8 carbon atoms, $R^2$ is hydrogen, or $R^1$ and $R^2$ together form an alkylene radical of 4 to 6 carbon atoms, and $R^3$, $R^4$, $R^5$ and $R^6$ are each hydrogen or methyl, are very particularly important as scents for the fine perfume industry. Particular examples are
2-methyl-5-formyl-1,3-dioxepan,
2-tert-butyl-5-formyl-1,3-dioxepan,
2-isopropyl-5-formyl-1,3-dioxepan,
2-pentyl-5-formyl-1,3-dioxepan,
2-pentyl-4,7-dimethyl-5-formyl-1,3-dioxepan,
2-propyl-5-formyl-1,3-dioxepan,
2-(2,4,4-trimethyl-pentyl)-5-formyl-1,3-dioxepan,
9-formyl-7,12-dioxaspiro[5.6]dodecane,
2,4,7-trimethyl-5-formyl-1,3-dioxepan and
2,4,4,7,7-pentamethyl-5-formyl-1,3-dioxepan.

EXAMPLE 1

Preparation of 2-tert-butyl-5-formyl-1,3-dioxepan

A. A mixture of 430 g (5 moles) of 2,2-dimethylpropanal, 3 g of p-toluenesulfonic acid and 440 g (5 moles) of but-2-ene-1,4-diol in 1000 ml of toluene was refluxed, and the water of reaction formed was removed in the course of 3 hours (h). The mixture was then left to cool to room temperature, 10 ml of a 25% strength sodium hydroxide solution were added to the solution, the mixture was washed neutral with a little water and the toluene was distilled off under reduced pressure at from 50° to 60° C. The residue obtained was distilled under 0.1 mbar to give 702 g of 2-tert-butyl-4,7-dihydro-1,3-dioxepin of boiling point 80° C./32 mbar.

B1. 430 mg of a 2-tert-butyl-4,7-dihydro-1,3-dioxepin prepared as described in A, 300 ml of toluene and 52 mg of (Rh(COD)CL)$_2$ (COD=cycloocta-1,5-dienyl) were initially taken in a 1 l autoclave equipped with a lift-type magnetic stirrer. Thereafter, a 1:1 CO/H₂ mixture was The compounds listed in Table 1 were prepared similarly to Example 1.

TABLE 1

| Example | Carbonyl compound | —4,7-dihydro-1,3-dioxepin | Bp. [°C./mbar] | —5-formyl-1,3-dioxepan | Bp. [°C./mbar] | $n_D^{25}$ | Description of odor |
|---|---|---|---|---|---|---|---|
| 1 | ⊥-CHO | 2-tert.-Butyl- | 80/32 | 2-tert.-Butyl- | 125/34 67/05 | 1,4569 | fresh sea breeze, lily of the valley |
| 2 | ⟩-CHO | 2-Isopropyl- | 75/32 | 2-Isopropyl- | 122/35 60/0.4 | 1,4517 | green woody |
| 3 | CH₃—CHO | 2-Methyl- | 145/ND | 2-Methyl- | 66/0.005 | 1,4523 | green fruity |
| 4 | (isobutoxy-acetaldehyde) | 2-[1'-Isobutoxy-ethyl]- | 71/0.3 | 2-[1'-Isobutoxyethyl]- | 100/2 | 1,4520 | very fresh ozone-like |
| 5 | (methyl tetrahydropyran CHO) | 2-[2,3,4,5,6-Pentahydro-4-methyl-pyran-3-yl]- | 95/0.3 | 2-[2,3,4,5,6-Pentahydro-4-methyl-pyran-3-yl]- | 145/0.05 | 1,4830 | floral |
| 6 | (bicyclic CHO) | 2(2,7,7-Trimethyl-bicyclo[3.1.1¹·⁵]-heptan-3-yl- | 120/0.3 | 2(2,7,7-Trimethyl-bicyclo[3.1.1¹·⁵]-heptan-3-yl- | 115.0.5 | 1,4929 | green, herbaceous |
| 7 | ~~~CHO | 2-Pentyl- | 78/30 | 2-Pentyl- | 100/0.01 | 1,4558 | herbaceous green, rhubarb note |
| 8 | ~~CHO | 2-Propyl- | 107/94 | 2-Propyl- | 65/0.2 | 1,4531 | sweet spicy, estragole-like |
| 9 | (cyclohexylidene ketone) | 7,12-Dioxa-spiro-[5.6]dodeca-9-en yl- | 105/5 | 9-Formyl-1,12-dioxa-spiro[5.6]dodecanyl- | 92/0.01 | 1,4832 | balsamic, sweetish, fruity |
| 10 | ⋌⋋CHO | 2-[2,4,4-Trimethyl-pentyl]- | 123/6 | 2-[2,4,4-Trimethyl-pentyl]- | 120/0.2 | 1,4562 | spicy, herbaceous | forced in at room temperature under 300 bar, the autoclave was heated to 90° C. and a CO/H₂ pressure of 650 bar was maintained for 12 h. The autoclave was cooled and let down, after which the reaction mixture was subjected to a short-path distillation. 456 g of 2-tert-butyl-5-formyl-1,3-dioxepan of boiling point 122° C./35 mbar were obtained. The product contained about 10% of the 4-formyl isomer, which could readily be separated off by distillation.

B2. 50 g of 2-tert-butyl-4,7-dihydro-1,3-dioxepin (prepared as described in A), 100 ml of toluene, 100 ppm of Rh in the form of (Rh(COD)Cl)₂ and 1 g of triphenylphospine were initially taken in a 300 ml stirred autoclave. A 1:1 CO/H₂ mixture was forced in at room temperature under 30 bar, the autoclave was heated to 90° C. and a pressure of 200 bar was maintained for 12 h. The mixture was worked up by distillation similarly to Example 1B1 to give 52 g of 5-formyl-2-tert-butyl-1,3-dioxepan of boiling point 124° C./35 mbar. The corresponding 4-formyl isomer was not detectable by gas chromatography.

EXAMPLE 11

Preparation of 2-propyl-4,7-dimethyl-5-formyl-1,3-dioxepan

A. A mixture of 580 g (5 moles) of hex-3-ene-2,5-diol, 3 g of p-toluenesulfonic acid, 360 g (5 moles) of n-butanal and 1 l of toluene was refluxed, and the resulting water of reaction (108 ml) was removed in the course of 3 h. Thereafter, the mixture was left to cool to room temperature, 10 ml of a 25% strength aqueous sodium hydroxide solution were added, the mixture was washed neutral with a little water and the toluene was removed under reduced pressure at from 50° to 60° C. The residue obtained was distilled under 0.1 mbar to give 681 g (4 moles) of 2-propyl-4,7-dimethyl-4,7-dihydro-1,3-dioxepin of boiling point 70° C./0.1 mbar.

B. 400 g of 2-propyl-4,7-dimethyl-4,7-dihydro-1,3-dioxepin (prepared as described in A), 300 ml of toluene and 52 mg of (Rh(COD)Cl)₂ were initially taken in a 1 l autoclave equipped with a lift-type magnetic stirrer. Therafter, a 1:1 CO/H₂ mixture was forced in at room temperature under 300 bar, the autoclave was heated to 90° C. and a CO/H$_2$ pressure of 650 bar was maintained for 12 h. The autoclave was cooled to let down, after which the reaction mixture was worked up by distillation in a short-path distillation apparatus to give 410 g of 2-propyl-4,7-dimethyl-5-formyl-1,3-dioxepan.

The compounds listed in Table 2 were prepared similarly to Examples 11 and 11A and Example 1B2.

of 2-pentyl-4,4,7,7-tetramethyl-4,7-dihydro-1,3-dioxepin of boiling point 75° C./0.1 mbar.

B. 40 g of 2-pentyl-4,4,7,7-tetramethyl-4,7-dihydro-1,3-dioxepin, 100 ml of toluene and 104 mg of (Rh(COD)Cl)$_2$ and 1 g of triphenylphosphine were initially taken in a 300 ml stirred autoclave. A 1:1 CO/H$_2$ mixture was forced in at room temperature under 30 bar, the autoclave was heated to 90° C. and a

TABLE 2

| Example | Carbonyl compound | —4,7-dimethyl-4,7-dihydro-1,3-dioxepin | Bp. [°C./mbar] | —4,7-dimethyl-5-formyl-1,3-dioxepan | Bp. [°C./mbar] | $n_D^{25}$ | Description of odor |
|---|---|---|---|---|---|---|---|
| 11 | ⌒⌒CHO | 2-Propyl- | 60/0.1 | 2-Propyl- | 63/0.1 | 1,4459 | green note, bean-like |
| 12 | ⌒⌒⌒CHO | 2-Pentyl- | 74/0.1 | 2-Pentyl- | 94/0.6 | 1,4487 | fresh, aldehyde-like |
| 13 | CH$_3$CHO | 2-Methyl- | 50/0.1 | 2-Methyl- | 55/0.3 | 1,4552 | calmus-like, spicy |
| 14 | ⌒⌒CHO | 2-[2,4,4-Trimethylpentyl]- | 90/0.01 | 2-[2,4,4-Trimethylpentyl]- | 99/0.001 | 1,4518 | ozone-like, fresh |
| 15 | (bicyclic)CHO | 2-(2,7,7-Trimethylbicyclo[3.1.1$^{1,5}$]-heptan-3-yl)- | 76/0.01 | 2-(2,7,7-Trimethylbicyclo[3.1.1$^{1,5}$]-heptan-3-yl)- | 117/0.001 | 1,4840 | herbaceous, celery-like |

EXAMPLE 16

Preparation of 2-pentyl-4,4,7,7-tetramethyl-5-formyl-1,3-dioxepan

A. A mixture of 720 g (5 moles) of 2,5-dimethylhex-3-ene-2,5-diol, 3 g of p-toluenesulfonic acid, 500 g (5 moles) of n-hexanal and 1 l of toluene was refluxed, and the resulting water of reaction (115 ml) was separated off in the course of 5.5 h. The mixture was then left to cool, 10 ml of a 25% strength aqueous sodium hydroxide solution were added, the mixture was washed neutral with a little water and the toluene was removed under reduced pressure at from 50° to 60° C. The residue obtained was distilled under 0.1 mbar to give 796 g pressure of 200 bar was maintained for 12 h. The mixture was worked up by distillation to give 41 g of 2-pentyl-5-formyl-4,4,7,7-tetramethyl-1,3-dioxepan of boiling point 130° C./0.005 mbar.

The compounds listed in Table 3 were prepared similarly to Example 16 or to Examples 16A and 1B1.

TABLE 3

| Example | Carbonyl compound | —4,4,7,7-tetramethyl-1,3-dioxepin | Bp. [°C./mbar] | —4,4,7,7-tetramethyl-5-formyl-1,3-dioxepan | Bp. [°C./mbar] | $n_D^{25}$ | Description of odor |
|---|---|---|---|---|---|---|---|
| 16 | ⌒⌒⌒CHO | 2-Pentyl- | 75/0.1 | 2-Pentyl- | 98/0.005 | 1,4552 | herbaceous, green |
| 17 | ⌒⌒CHO | 2-Propyl- | 60/0.1 | 2-Propyl- | 86/0.15 | 1,4535 | woody note |
| 18 | CH$_3$—CHO | 2-Methyl- | 50/0.1 | 2-Methyl- | Mp. 78° C. | — | oakmoss-like |
| 19 | ⌒⌒CHO | 2-[2,4,4-Trimethylpentyl]- | 81/0.1 | 2-[2,4,4-Trimethylpentyl]- | 124/0.015 Mp. 49° C. | — | green note, bean-like |
| 20 | ⊣CHO | 2-tert.-Butyl- | 74/18 | 2-tert.-Butyl- | 68/0.005 | 1,4551 | fresh aldehyde note |
| 21 | ⟩—CHO | 2-Isopropyl- | 74/13 | 2-Isopropyl- | 82/0.01 Mp. 44° C. | — | sweetish, fruity |
| 22 | O⌒CHO | 2-Methoxymethyl- | 46/0.015 | 2-Methoxymethyl- | 98/0.035 | 1,4580 | floral, fresh |

EXAMPLE OF USE

The important possible uses of the novel compounds will be indicated by the effect of 2-tert-butyl-5-formyl-1,3-dioxepan on a known flower base.

Example A: Classical muguet base no. 1 (from E. V. Wells and M. Billot, Perfumery Technology, John Wiley & Sons, 2nd Ed. 1981, page 223)

|  | A Parts by weight | B Parts by weight |
|---|---|---|
| Citronellol | 33.7 | 33.7 |
| Rhodinol P | 11.3 | 11.3 |
| Phenylethanol | 24.7 | 24.7 |
| Hydroxycitronellal | 14.6 | 10.0 |
| Benzyl benzoate | 6.7 | 6.7 |
| Diethyl phthalate | 4.5 | 4.5 |
| α-amylcinnamaldehyde | 2.25 | 2.25 |
| Indole 10% | 2.25 | 2.25 |
| 2-tert-butyl-5-formyl-1,3-dioxepan | — | 4.6 |
| | 100 | 100 |

When 4.6 parts of hydroxycitronellal are replaced with 2-tert-butyl-5-formyl-1,3-dioxepan, the muguet base (B) has a stronger, more well rounded and considerably fresher effect.

We claim:
1. 2-isopropyl-5-formyl-1,3-dioxepan.
2. 2-propyl-5-formyl-1,3-dioxepan.
3. 2-(2,4,4-trimethyl-pentyl)-5-formyl-1,3-dioxepan.
4. 2-pentyl-4,7-dimethyl-5-formyl-1,3-dioxepan.
5. 2,4,7-trimethyl-5-formyl-1,3-dioxepan.
6. 2,4,4,7,7-pentamethyl-5-formyl-1,3-dioxepan.
7. 2-tert-butyl-5-formyl-1,3-dioxepan.

* * * * *